United States Patent [19]

Fujita et al.

[11] Patent Number: 5,532,125

[45] Date of Patent: Jul. 2, 1996

[54] METHOD FOR ASSAYING NUCLEIC ACIDS

[75] Inventors: Satoshi Fujita; Naoto Kagiyama; Masayoshi Momiyama, all of Sapporo, Japan

[73] Assignee: Aisin Seiki Kabushiki Kaisha, Japan

[21] Appl. No.: 44,098

[22] Filed: Apr. 6, 1993

Related U.S. Application Data

[63] Continuation of Ser. No. 738,517, Jul. 31, 1991, abandoned.

[30] Foreign Application Priority Data

Aug. 7, 1990 [JP] Japan ..................... 2-210055

[51] Int. Cl.$^6$ ............... C12Q 1/68; C12Q 1/42
[52] U.S. Cl. ................. 435/6; 435/772; 435/21; 548/113
[58] Field of Search ............... 435/6, 7.6, 7.72, 435/21; 436/800; 534/573; 548/113; 558/9, 193

[56] References Cited

U.S. PATENT DOCUMENTS

| | | | |
|---|---|---|---|
| 3,140,283 | 7/1964 | Depoorter et al. | 260/240 |
| 3,180,873 | 4/1965 | Schmidt et al. | 260/313 |
| 4,582,789 | 4/1986 | Sheldon, III et al. | 435/6 |
| 4,617,261 | 10/1986 | Sheldon, III et al. | 435/6 |
| 4,705,886 | 11/1987 | Levenson et al. | 560/159 |
| 4,751,313 | 6/1988 | Levenson et al. | 548/303 |
| 4,754,065 | 6/1988 | Levenson et al. | 562/564 |
| 4,803,297 | 2/1989 | Levenson et al. | 860/159 |
| 4,889,798 | 12/1989 | Rabbani | 435/6 |

FOREIGN PATENT DOCUMENTS

| | | |
|---|---|---|
| 0124124A2 | 11/1984 | European Pat. Off. . |
| 0154788A2 | 9/1985 | European Pat. Off. . |
| 0401813A2 | 12/1990 | European Pat. Off. . |
| 4041880A1 | 7/1991 | Germany . |
| 60-226888 | 11/1985 | Japan . |
| 1-160990 | 6/1989 | Japan . |
| 2239948 | 7/1991 | United Kingdom . |
| WO87/04165 | 7/1987 | WIPO . |

OTHER PUBLICATIONS

Burstone, M. S., Enzyme Histochemistry and Its Application in the Study of Neoplasms, pp. 64–67, 82–83 (Academic Press, 1962).
Chemical Abstracts, 55, abstract No. 10550 (g) (1961).
Chemical Abstracts, 115(25): abstract No. 275243v (1991).
Mullink, H., et al., "Combined Immuno–and Non–radioactive Hybridocyto–chemistry on Cells and Tissue Sections: Influence of Fixation, Enzyme Pre–treatment, and Choice of Chromogen on Detection of Antigen and DNA Sequences," The Journal of Histochemistry and Cytochemistry, 37(5): 603–609 (1989); Chemical Abstracts, 110: 228120q (1989).
Römpp Chemie Lexikon, pp. 3375–3376 (9th ed.) Date Not Avail.
Vaughan, A., et al., "Fluorometric Methods for Analysis of Acids and Alkaline Phosphatase," Analytical Chemistry, 43(6): 721–724 (1971).
West, S., et al., "A Multiple–Staining Procedure for the Detection of Different DNA Fragments on a Single Blot," Analytical Biochemistry, 190: 254–258 (1990).

*Primary Examiner*—Ralph J. Gitomer
*Attorney, Agent, or Firm*—Finnegan, Henderson, Farabow, Garrett & Dunner

[57] ABSTRACT

A method for assaying nucleic acids or similar compounds comprises binding a sample such as a nucleic acid to phosphatase; reacting the phosphatase with a 3-hydroxy-2-naphthoic acid-2'-phenyl anilide phosphate; irradiating the reaction product with an excited light; and detecting fluorescence emitted therefrom.

1 Claim, 1 Drawing Sheet

METHOD FOR ASSAYING NUCLEIC ACIDS

This application is a continuation, of application Ser. No. 07/738,517 filed Jul. 31, 1991, now abandoned.

BACKGROUND OF THE INVENTION

1. Field of the Invention

The present invention describes an efficient method for assaying nucleic acids employing fluorescence.

2. Related Art

In medical and biological fields, a DNA or RNA probe complexed with a radioactive isotope has been employed as a means of detecting nucleic acids. This technique comprises hybridizing the labeled probe with a target nucleic acid, followed by detecting the target nucleic acid by autoradiography. This isotope method has numerous drawbacks which are serious obstacles to the application and development of this technology. The drawbacks of the isotope method are as follows:

(a) The nucleic acid hybridization method lacks spatial resolution sufficient to reveal the relative positional relationship between contiguous signals.

(b) Experimental procedures using isotope can only be performed in isotope laboratories equipped with special facilities. This hinders the application of the hybridization method, particularly for clinical applications.

(c) Use of isotope is dangerous for laboratory workers even under controlled laboratory conditions. In addition, a danger for non-laboratory workers also exists because of radioactive wastes.

(d) An extended period (several weeks to several months) may be required for detection, such that application to rapid clinical diagnosis is difficult.

(e) Radioactivity decays with a definite half-life period. Accordingly, experiments must be scheduled around a purchase date of isotope. If the schedule chart is slightly altered, there is a danger of wasting isotope or experimental results on a large scale.

(f) To enhance detection sensitivity, significant quantities of radioactivity must be incorporated in a nucleic acid probe. However, this highly radioactive nucleic acid is unstable and easily suffers from radioactive disintegration.

(g) In general, isotope is extremely expensive. This prevents general use of the hybridization method.

In view of such drawbacks, DNA or RNA labeling methods in place of employing radioactive isotope have been developed. For example, BLU GENE KIT™, commercially available from Bethesda Research Laboratories Inc. (BRL Inc.), is known. Additionally, "Nucleic Acid Probe And Use Thereof" is disclosed in Japanese Patent Application Laid-Open No. 60-226888.

However, these techniques do not eliminate all of the drawbacks described above. In particular, detection sensitivity is not comparable to that of the isotope method. In the above labeling, the detection sensitivity is "$10^{-12}$ g DNA," slightly inferior to the "$10^{-13}$ g DNA" of the isotope method.

An object of the present invention is to provide a method for assaying nucleic acids which eliminates the drawbacks of the isotope method and which also provides excellent detection sensitivity.

SUMMARY OF THE INVENTION

The present invention provides a method for assaying nucleic acids or similar compounds comprising binding phosphatase to a sample (e.g. nucleic acids), reacting the phosphatase with 3-hydroxy-2-naphthoic acid-2'-phenyl anilide phosphate, irradiating the reaction products with an excited light, and detecting the fluorescence emitting therefrom.

DETAILED DESCRIPTION OF PREFERRED EMBODIMENTS

It is preferable in the present invention to employ a 3-hydroxy-2-naphthoic acid-2'-phenyl anilide phosphate to which a phosphatase is bound. Examples of phosphatases include alkali phosphatase and acid phosphatase.

Sample compounds which can be detected by the method of the present invention comprise nucleic acid (DNA or RNA), protein, and immunological detection of a chemical compound using antibody.

An example of a 3-hydroxy-2-naphthoic acid-2'-phenyl anilide phosphate includes the basic skeleton shown by Formula (I).

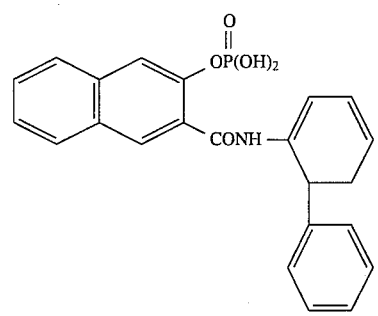

In the assay method according to the present invention, a 3-hydroxy-2-naphthoic acid-2'-phenyl anilide phosphate is reacted with a phosphatase, followed by irradiation with an excited light, whereby the dephosphating product of the 3-hydroxy-2-naphthoic acid-2'-phenyl anilide phosphate emits fluorescence. The emitted fluorescence can then be detected.

The 3-hydroxy-2-naphthoic acid-2'-phenyl anilide phosphate is reacted with a phosphatase combined with a sample (e.g. nucleic acids) on a membrane filter made of nylon. This produces a dephosphating product of the 3-hydroxy-2-naphthoic acid-2'-phenyl anilide phosphate, which adheres to the nylon membrane filter and displays fluorescence. The fluorescence and the pattern thereof (spots, and bands produced by electrophoresis) are then detected by irradiation with an excited light.

In the present invention, intense fluorescence can be obtained by employing a 3-hydroxy-2-naphthoic acid-2'-phenyl anilide phosphate to improve detection sensitivity; for example, $3 \times 10^{-14}$ g (0.03 pg) of DNA is detectable. No isotope is used in this method, and therefore, the drawbacks of the prior art are eliminated.

Thus, a method for assaying nucleic acids or similar compounds which provides excellent detection sensitivity is described. Further, the present invention provides the dephosphating product of a 3-hydroxy-2-naphthoic acid-2'-phenyl anilide phosphate in a high yield.

EXAMPLES

Example 1

To verify the effectiveness of a 3-hydroxy-2-naphthoic acid-2'-phenyl anilide phosphate as a probe for nucleic acids, the DNA Labeling and Detection Kit of Boehringer Mannheim and 3-hydroxy-2-naphthoic acid-2'-phenyl anilide phosphate were used to detect DNA on a nylon membrane filter.

Figure 1:
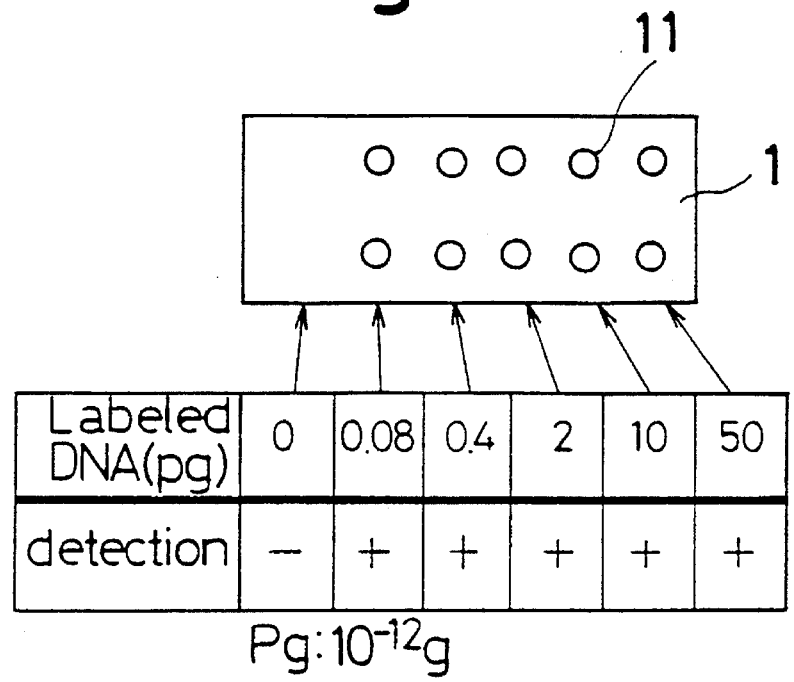
FIG. 1 shows the test results obtained in Example 1.

DNA was labeled with digoxigenin (Dig), diluted, and spotted on the nylon membrane filter. Each of the spots included 50 ng ($50 \times 10^{-9}$ g) DNA of herring spermatozoa. 0.08 to 25 pg of Dig-labeled DNA was employed. The results are shown in FIG. 1. 0 pg in the Figure represents a blank test. Reference numeral 1 designates a carrier filter for a specimen of nucleic acids, and reference numeral 11 designates fluorescence sensitized portions. "+" represents detection of DNA; "±" represents that DNA cannot distinctly be detected; and "−" represents that DNA cannot be detected. The results shown in FIG. 1 demonstrate that DNA could satisfactorily be detected in 0.08 pg of sample.

Figure 2:
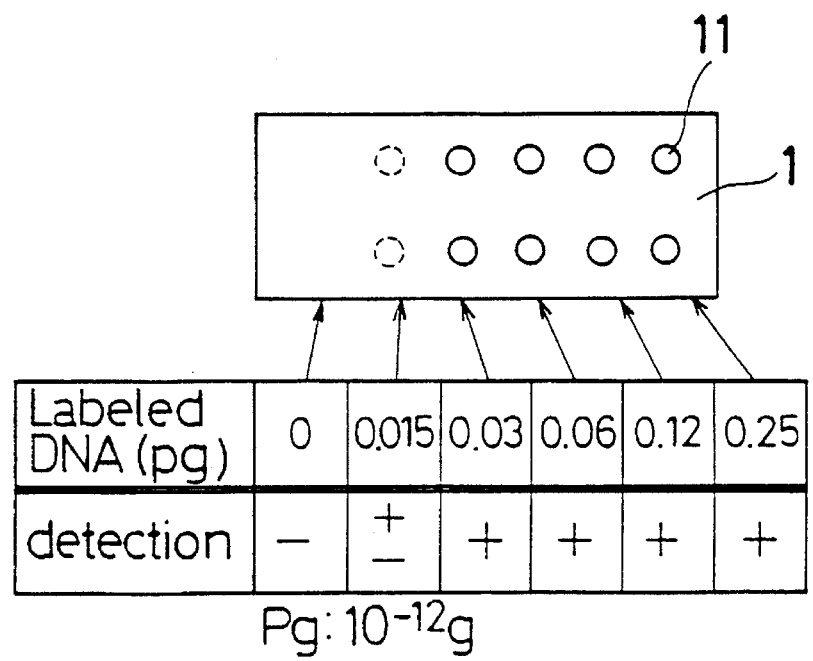
FIG. 2 shows the test results obtained in Example 1.

Using a smaller amount of DNA, a second experiment was conducted on 0.015 to 0.25 pg of Dig-labeled DNA in the same manner as described above. The test results are shown in FIG. 2. Satisfactory detection was obtained in a 0.03 pg (30 fg) sample.

In the first experiment, a conventional color development detection using azo-color, Fast Blue BB™ (of POLYSCIENCE, INC.) was employed. The detectable spot included 0.5 pg ($0.5 \times 10^{-12}$ g) of DNA.

Example 2

A 3-hydroxy-2-naphthoic acid-2'-phenyl anilide phosphate was produced by the following processes.

According to the description of Enzyme Histochemistry, 5 g (0.027 mol) of 2-hydroxy-3-naphthoic acid, 40 ml of dehydrated xylene, and 0.023 mol of 3,5-dimethyl aniline were stirred in a 100 ml NASU flask provided with a Graham condenser at 80° C. for 10 minutes. 0.01 mol of phosphorous trichloride was then added to the flask and the resultant mixture was refluxed for 2 hours. Thereafter, the reaction solution was decanted in the hot state to skim the supernatant fluid. After cooling the fluid at 4° C., the fluid was filtered, and the precipitates thus obtained were eluted with xylene and then water. The precipitates were then neutralized with a 2% aqueous solution of sodium carbonate, and xylene was removed from the precipitates by boiling.

The precipitates were brought to pH 9 with a 2% aqueous solution of sodium carbonate, filtered, and cooled. The precipitates thus obtained were eluted with water and added to a 3% HCl solution, heated, filtered, and cooled. The precipitates were then washed with hot water and dried.

Next, the precipitates were recrystalized to produce 3-hydroxy-2-naphthoic acid-2'-biphenyl anilide, shown by the following formula (II).

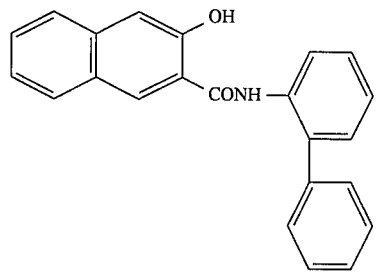

1 g of this naphthol AS derivative was dissolved in 8 ml of pylidine. After stirring this solution at 0° C. for 30 minutes, phosphorus oxychloride (2.5 eg), cooled similarly, was added and stirred at 0° C. for 4 hours. Ice was then added to the solution to terminate the reaction.

The reaction product obtained was purified on a reverse phase silica gel column, followed by purification on a normal phase silica gel column, to produce 3-hydroxy-2-naphthoic acid-2'-phenyl anilide phosphate, shown by the following formula (III).

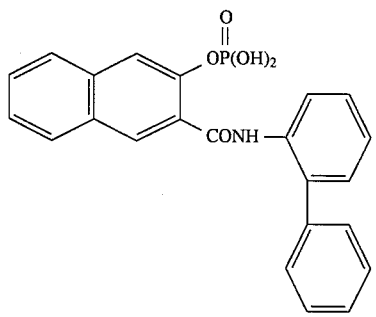

What is claimed is:

1. A method for determining a presence of nucleic acid in a sample, comprising
   (A) contacting phosphatase with said sample, such that any nucleic acid in said sample binds to phosphatase to form a modified phosphatase;
   (B) contacting any modified phosphatase produced in step (A) with a 3-hydroxy-2-naphthoic-acid-2'-phenyl anilide phosphate to form a reaction product;
   (C) irradiating said reaction product with an excited light source; and
   (D) detecting any fluorescence produced in step (C);
   wherein nucleic acid is determined to be present if fluorescence is detected.

* * * * *